(12) United States Patent
Struble

(10) Patent No.: US 6,466,824 B1
(45) Date of Patent: Oct. 15, 2002

(54) BI-ATRIAL AND/OR BI-VENTRICULAR PATIENT SAFETY CABLE AND METHODS REGARDING SAME

(75) Inventor: Chester L. Struble, Eijsden (NL)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/839,303

(22) Filed: Apr. 23, 2001

(51) Int. Cl.[7] .................................................. A61N 2/02
(52) U.S. Cl. ....................................................... 607/115
(58) Field of Search ................................ 607/115, 122, 607/123

(56) References Cited

U.S. PATENT DOCUMENTS

| | | |
|---|---|---|
| 4,341,226 A | 7/1982 | Peters |
| 5,241,957 A | 9/1993 | Camps et al. |
| 5,403,353 A | 4/1995 | Alferness et al. |
| 5,626,621 A | 5/1997 | Skoglund et al. |
| RE35,779 E | 4/1998 | Alferness et al. |
| 5,766,224 A | 6/1998 | Alferness et al. |
| 5,902,324 A | 5/1999 | Thompson et al. |
| 5,931,861 A | 8/1999 | Werner et al. |
| 6,070,101 A | 5/2000 | Struble et al. |
| 6,081,748 A | 6/2000 | Struble et al. |
| 6,122,545 A | 9/2000 | Struble et al. |
| 6,141,589 A | 10/2000 | Duhaylongsod |

*Primary Examiner*—Scott M. Getzow
(74) *Attorney, Agent, or Firm*—Thomas F. Woods; Eric R. Waldkoetter; Tom G. Berry

(57) ABSTRACT

A bi-atrial and/or bi-ventricular patient safety cable includes a multi-conductor insulated external cable having a Y-connector portion, an external lead connector assembly, and two or more lead adaptors. The patient safety cable is used to electrically connect one or more implantable leads "in parallel" to an external medical device.

28 Claims, 11 Drawing Sheets

BI-ATRIAL AND/OR BI-VENTRICULAR PATIENT SAFETY CABLE AND METHODS REGARDING SAME

FIELD OF THE INVENTION

The present invention relates to patient safety cables. More particularly, the present invention pertains to bi-atrial and/or bi-ventricular patient safety cables such as for use with implantable leads and external medical devices and methods for their use.

BACKGROUND OF THE INVENTION

The earliest instances of relatively prolonged cardiac stimulation, namely cardiac pacing, of a patient's heart was effected through implanted cardiac leads attached to the heart muscle at distal electrode ends and extended through an incision in the patient's skin. Initially, cardiac pacing was employed during postoperative recovery from cardiac surgery, and the attachment to the heart was made to the epicardium during the surgical procedure. To effect unipolar pacing of the heart, a single such implantable pacing lead was employed in conjunction with a subcutaneously implanted or skin surface return electrode coupled to an external lead conductor. To effect bipolar pacing of the heart, two such implantable pacing leads were implanted with the electrode ends implanted a distance apart. Implantable pacing leads have since evolved, for example, into permanent, unipolar and/or bipolar, endocardial and epicardial, pacing leads for chronic implantation in a patient.

Various circumstances require the connection of an external medical device to an implantable lead system, such as a system including unipolar and/or bipolar leads. Generally, cables are used to provide such connections. For example, such a situation arises during surgical implantation of an implantable device, e.g., a pacemaker or pacemaker-cardioverter-defibrillator, including a permanent cardiac lead or lead system, or, for example, during connection of a replacement implantable device with a pre-existing permanent cardiac lead or lead system. One particular situation includes an external pacing system analyzer, e.g., the MEDTRONIC® Model No. 5311 B PSA, that may be attached to the lead system to assess the performance thereof.

Further, for example, during patient hospitalization, a lead system may be implanted to allow monitoring and demand pacing of the heart as the patient recovers from cardiac surgery or another condition. It may be necessary at times to connect the lead system implanted in a patient to a temporary external pacemaker, programmer, analyzer, or other external medical device. For example, the proximal ends of the lead system may be attached to external medical device connector elements associated with MEDTRONIC® Model Nos. 5348 or 5388 external single chamber or dual chamber cardiac pacemakers. When a permanent or temporary pacing lead is to be connected, for example, a MEDTRONIC® Model 5433AN or the Model 5832/S reusable safety cable may be employed to make the connection between the temporary pacemaker and the proximal connector ends of the pacing lead.

In addition, the proximal ends of the lead system may be attached to the external medical device connector elements associated with the MEDTRONIC® Model No. 9790 Programmer. Connection to the programmer may be accomplished by using the MEDTRONIC® Model No. 5436 Analyzer Patient Cable, which is designed to connect the programmer's analyzer subsystem to IS-1 implantable leads. The 5436 cable has two quick-connect bipolar lead connectors for dual chamber pacing and a spade-shaped indifferent electrode for unipolar pacing.

Recently, it has been proposed that various conduction disturbances involving both bradycardia and tachycardia of a heart chamber could benefit from stimulation applied at multiple electrode sites positioned in or about it in synchrony with a depolarization that has been sensed at at least one of the electrode sites. A number of proposals have been advanced for providing pacing therapies to alleviate these types of conditions and restore synchronous depolarization of right and left, upper and lower heart chambers. For example, commonly assigned U.S. Pat. No. 6,122,545, herein incorporated by reference, provides a multi-chamber cardiac pacing system method for providing synchronous pacing to the two upper heart chambers, to the two lower heart chambers, to three heart chambers, or to all four heart chambers. Such pacing systems require bi-atrial and/or bi-ventricular lead systems. These lead systems, in circumstances such as those described above, e.g., during hospitalization, may require operative connection to external devices, e.g., analyzer, external pacemaker, etc., for use in performing bi-atrial and/or bi-ventricular sensing/pacing functions. For example, during implant evaluation of bi-atrial and/or bi-ventricular configurations, sensing is analyzed and thresholds and impedances must be measured. Such measurements can be done in different configurations, namely single unipolar, single bipolar, common ring bipolar, etc.

The above-mentioned cables are designed to work with leads implanted in a single atrial and/or single ventricular chamber. For example, the MEDTRONIC® Model No. 5436 Analyzer Patient Cable is designed to connect an analyzer subsystem to two IS-1 implantable leads, e.g., one atrial lead and one ventricular lead. The cable has two quick-connect bipolar lead connectors and a spade-shaped indifferent electrode for unipolar pacing. The cable, however, is not suitable for use in bi-atrial and/or bi-ventricular sensing or pacing.

The systems and apparatus listed in Table 1 below, some of which are also described above, do not address the bi-atrial and/or bi-ventricular pacing/sensing problems discussed above, e.g., the inability to operatively connect bi-atrial and/or bi-ventricular implantable leads with an external medical device.

TABLE 1

| U.S. Pat. No. | Inventor | Issue Date |
| --- | --- | --- |
| 6,122,545 | Struble et al. | Sep. 19, 2000 |
| 6,081,748 | Struble et al. | Jun. 27, 2000 |
| 6,070,101 | Struble et al. | May 30, 2000 |
| 5,931,861 | Werner et al. | Aug. 3, 1999 |
| 5,902,324 | Thompson et al. | May 11, 1999 |
| 5,626,621 | Skoglund et al. | May 6, 1997 |
| 4,341,226 | Peters | Jul. 27, 1982 |

All references listed in Table 1, and elsewhere herein, are incorporated by reference in their respective entireties. As those of ordinary skill in the art will appreciate readily upon reading the Summary of the Invention, Detailed Description of the Embodiments, and claims set forth below, at least some of the devices and methods disclosed in the references of Table 1 and elsewhere herein may be modified advantageously by using the teachings of the present invention. However, the listing of any such references in Table 1, or elsewhere herein, is by no means an indication that such references are prior art to the present invention.

SUMMARY OF THE INVENTION

The present invention has certain objects. That is, various embodiments of the present invention provide solutions to one or more problems existing in the art with respect to patient safety cables. One such problem involves the inability to operatively connect bi-atrial and/or bi-ventricular implantable leads with an external medical device.

The bi-atrial and/or bi-ventricular patient safety cable and methods according to the present invention provide one or more of the following advantages. For instance, the present invention provides an "in-parallel" configured cable that operatively connects bi-atrial and/or bi-ventricular implantable leads (e.g., those leads used for multi-site pacing) with an external medical device. As such, for example, simultaneous pacing and sensing can be performed in both atrial chambers and/or both ventricular chambers.

Embodiments of an apparatus of the present invention may provide one or more of the following features: a patient safety medical device cable apparatus; a multi-conductor insulated external cable including a first cable portion, a second cable portion including at least one pair of external cable lead elements, and a Y-connector portion connected to a first end of the first cable portion; at least one pair of lo external cable lead elements that corresponds to one of a pair of bi-atrial implantable leads and a pair of bi-ventricular implantable leads; a Y-connector portion that includes at least one Y connection electrically connecting at least one pair of external cable lead elements with one or more conductors of a first cable portion; an external lead connector assembly electrically coupled to a second end of a first cable portion and configured to be electrically connected to an external medical device; two or more lead adaptors that are each configured for electrical connection to an implantable lead; external cable lead elements that are each terminated by a lead adaptor; an indifferent electrode lead element associated with at least a first cable portion and configured to be electrically connected with a patient; a second cable portion including a single pair of external cable lead elements, wherein the single pair of external cable lead elements corresponds to a single pair of bi-atrial implantable leads; a second cable portion including a single pair of external cable lead elements, wherein the single pair of external cable lead elements corresponds to a single pair of bi-ventricular implantable leads; a second cable portion including two pairs of external cable lead elements, wherein the two pairs of external cable lead elements correspond to a single pair of bi-atrial implantable leads and a single pair of bi-ventricular implantable leads; an external pacemaker including a connector assembly configured to mate with an external lead connector assembly; a programmer including a connector assembly configured to mate with an external lead connector assembly; and an analyzer including a connector assembly configured to mate with an external lead connector assembly.

Other embodiments of a method of the present invention may provide one or more of the following features: a method for electrically connecting one or more implantable leads to an external medical device; providing a patient safety medical device cable apparatus; providing a multi-conductor insulated external cable; providing an external cable including a first cable portion, a second cable portion including at least one pair of external cable lead elements corresponding to one of a pair of bi-atrial implantable leads and a pair of bi-ventricular implantable leads, and a Y-connector portion including at least one Y-connection electrically connecting at least one pair of external cable lead elements with one or more conductors of the first cable portion; providing an external lead connector assembly; providing two or more lead adaptors; attaching at least one lead adaptor to at least one implantable lead of a pair of bi-atrial implantable leads or a pair of bi-ventricular implantable leads; attaching an external lead connector assembly to an external medical device; and providing an indifferent electrode lead element associated with at least a first cable portion and configured to be electrically connected with a patient.

The above summary of the invention is not intended to describe each embodiment or every implementation of the present invention. Rather, a more complete understanding of the invention will become apparent and appreciated by reference to the following detailed description and claims in view of the accompanying drawings.

BRIEF DESCRIPTION OF THE DRAWINGS

The present invention will be further described with reference to the drawings, wherein.

DETAILED DESCRIPTION OF THE EMBODIMENTS

In the following detailed description of the embodiments, reference is made to the accompanying drawings which form a part hereof, and in which are shown by way of illustration specific embodiments in which the invention may be practiced. It is to be understood that other embodiments may be utilized and structural changes may be made without departing from the scope of the present invention.

Figure 1:
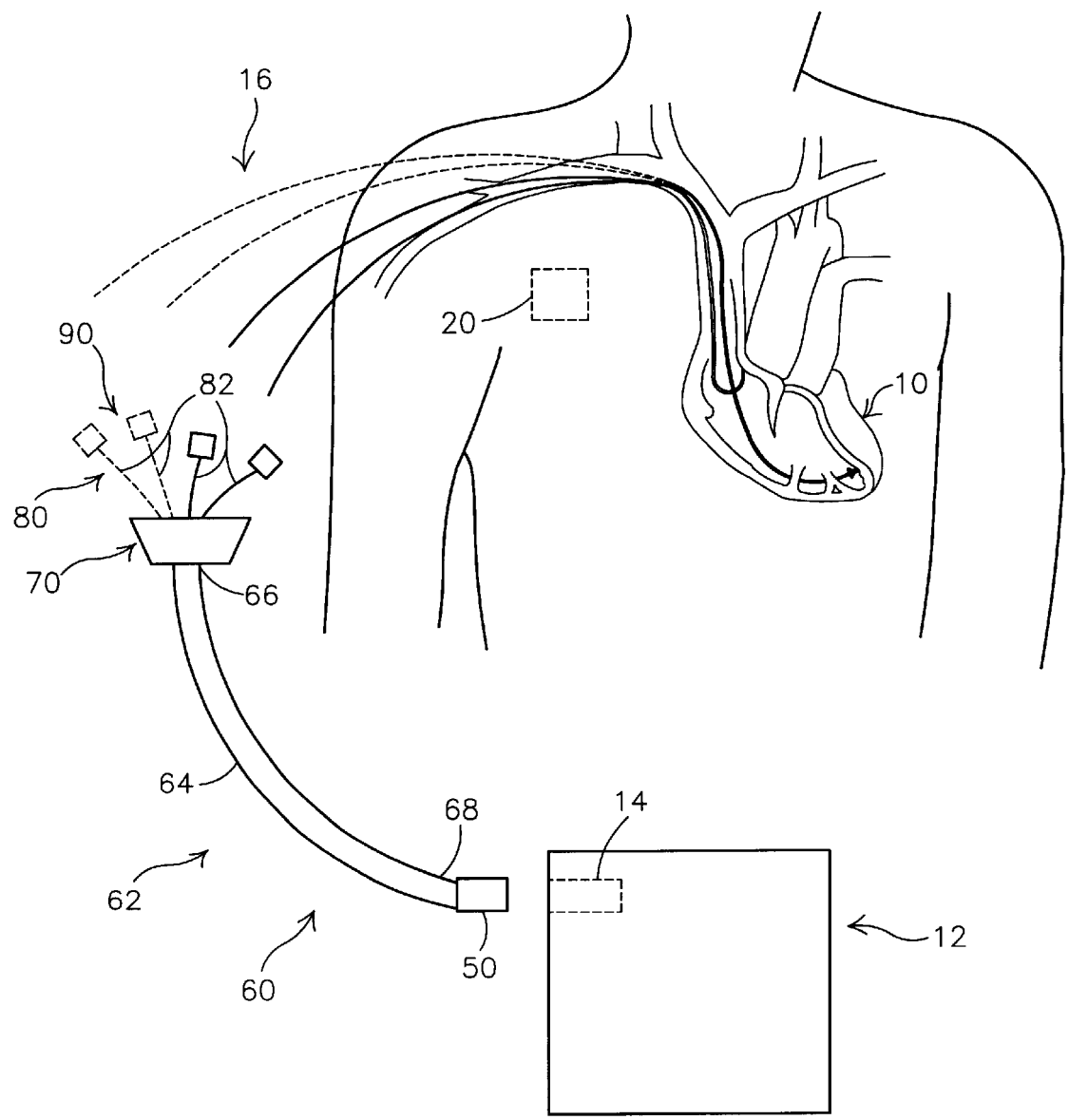
FIG. 1 is a general view of a patient safety medical device cable apparatus in accordance with the present invention, wherein the apparatus is shown in relation to a human body.

The present invention shall first be described generally with reference to FIG. 1. Various embodiments of the present invention shall be described with reference to FIGS. 2–12.

FIG. 1 generally illustrates a cable apparatus 60 in accordance with the present invention. The patient safety cable apparatus 60 is used for connecting an external medical device 12, e.g., a programmer, to one or more implantable leads 16 (e.g., bi-atrial and/or bi-ventricular leads). As illustrated therein, implantable leads 16 are located within the patient's body and extend beyond the body externally. The implantable leads 16 are shown implanted within the heart 10. The implantable leads 16 may be permanently implanted in the patient for use with an implantable medical device 20 (IMD). While illustrated as a cardiac IMD, cable systems in accordance with the present invention are equally applicable to IMDs of most any purpose, e.g., neurologic implants, nerve stimulators, muscle stimulators, or other similar devices. Alternatively, the implantable leads 16 may be temporarily implanted for monitoring by an external medical device 12 and then later removed.

Depending on the particular cardiac needs, e.g., two chamber pacing/sensing or four chamber pacing/sensing, the number of implantable leads may vary as further described below. The implantable leads 16, which are used to sense electrical signals attendant to the depolarization and re-polarization of cardiac tissue in the vicinity of the distal ends thereof, may have unipolar or bipolar electrodes disposed thereon, as is well known in the art.

Figure 2:
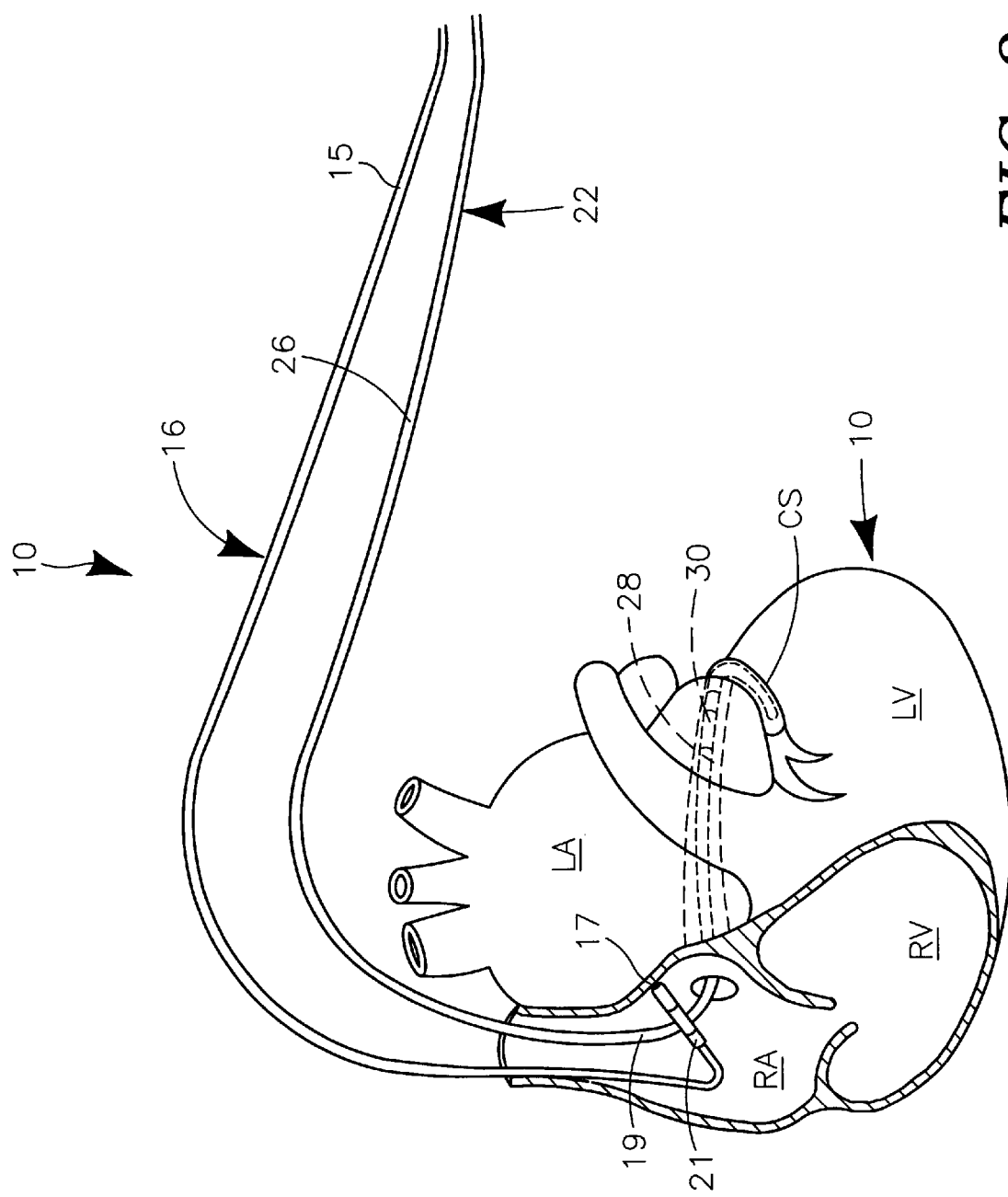
FIG. 2 is a diagram depicting a two channel, bi-atrial implantable lead system with which the present invention may be employed.

For example, FIG. 2 is an illustrative, exemplary representation of a bi-atrial implantable lead system. In FIG. 2, heart 10 includes the upper heart chambers, the right atrium (RA) and left atrium (LA), and the lower heart chambers, the right ventricle (RV) and left ventricle (LV) and the coronary sinus (CS) extending from the opening in the right atrium laterally around the atria to form the great vein that extends further inferiorly into branches of the great vein. Bipolar, endocardial implantable RA lead 16 and bipolar endocardial implantable LA CS lead 22 are passed through a vein into the RA chamber of the heart 10 and into the CS to extend alongside the LA chamber. The RA lead 16 may include a pair of electrically insulated conductors within lead body 15 and may be connected with distal tip RA pace/sense electrode 19 and proximal ring RA pace/sense electrode 21. The distal end of the RA lead 16 is attached to the RA wall by an attachment mechanism 17. The LA CS lead 22 is coupled to a pair of electrically insulated conductors within lead body 26 and connected with distal ring LA CS pace/sense electrode 30 and proximal ring LA CS pace/sense electrode 28. The distal end of the LA CS implantable lead 26 is extended into the CS to position the LA CS pace/sense electrodes optimally with respect to the adjacent LA wall.

Figure 3:
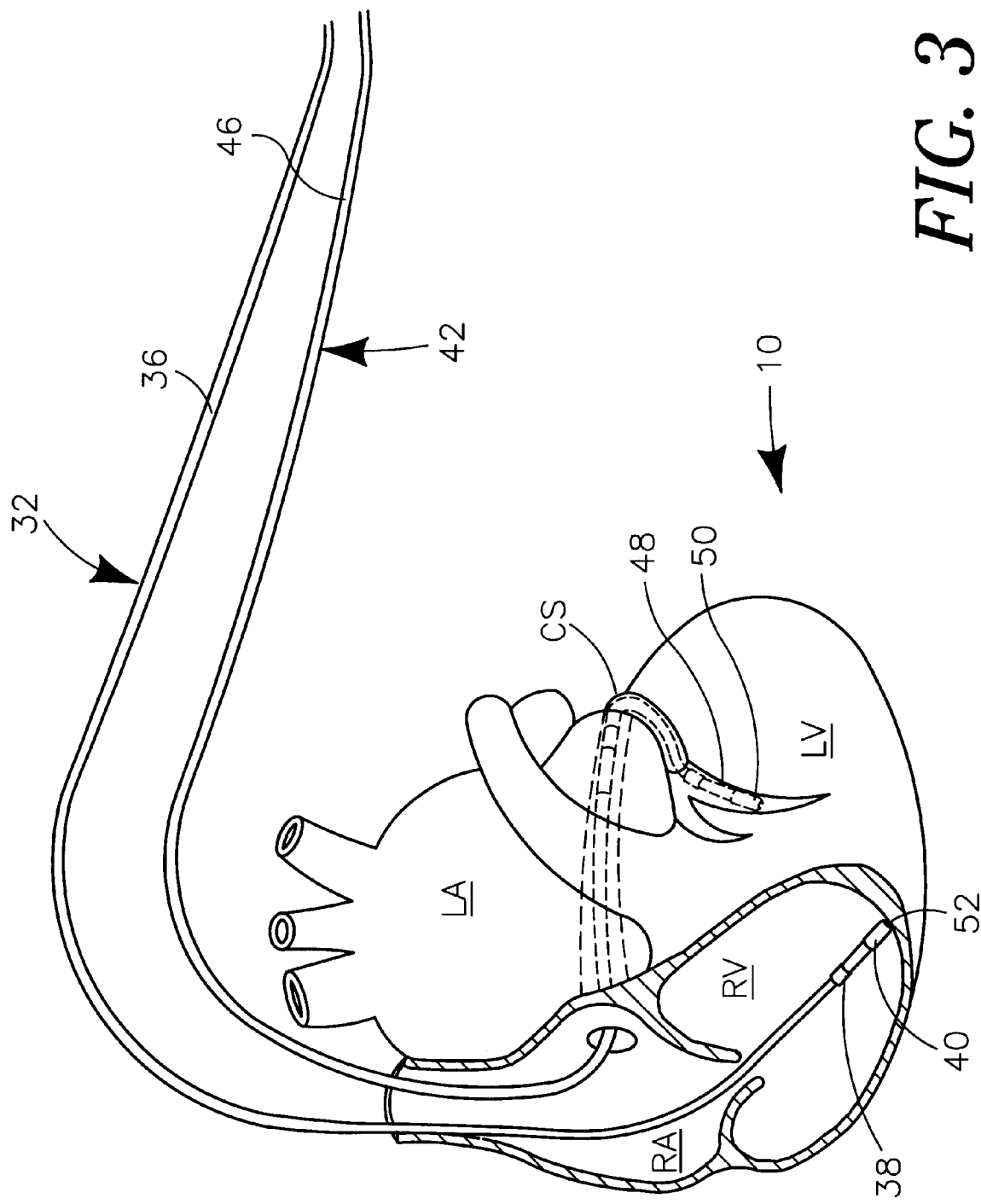
FIG. 3 is a diagram depicting another implantable lead system with which the present invention may be employed.

Further, FIG. 3 is an illustrative, exemplary representation of a bi-ventricular implantable lead system. Bipolar, endocardial LV CS lead 42 is passed through a vein into the RA chamber of the heart 10, into the CS and then inferiorly in the great vein and cardiac veins extending therefrom to extend the distal ring pace/sense electrodes 48 and 50 alongside the LV chamber. Bipolar, endocardial RV lead 32 is passed through the vein into the RA chamber of the heart 10 and into the RV where its distal ring and tip pace/sense electrodes 38 and 40 are fixed in place in the apex or in the interventricular septum by a distal attachment mechanism 52. The RV lead 32 is coupled to a pair of electrically insulated conductors within lead body 36 and connected with distal tip pace/sense electrode 40 and proximal pace/sense ring electrode 38. The LV CS lead 42 is coupled to a pair of electrically insulated conductors within lead body 46 and connected with distal ring pace/sense electrode 50 and proximal pace/sense ring electrode 48. The distal end of the LV CS lead 42 is extended into the CS to position the ring electrodes optimally with respect to the adjacent LV wall.

Figure 4:
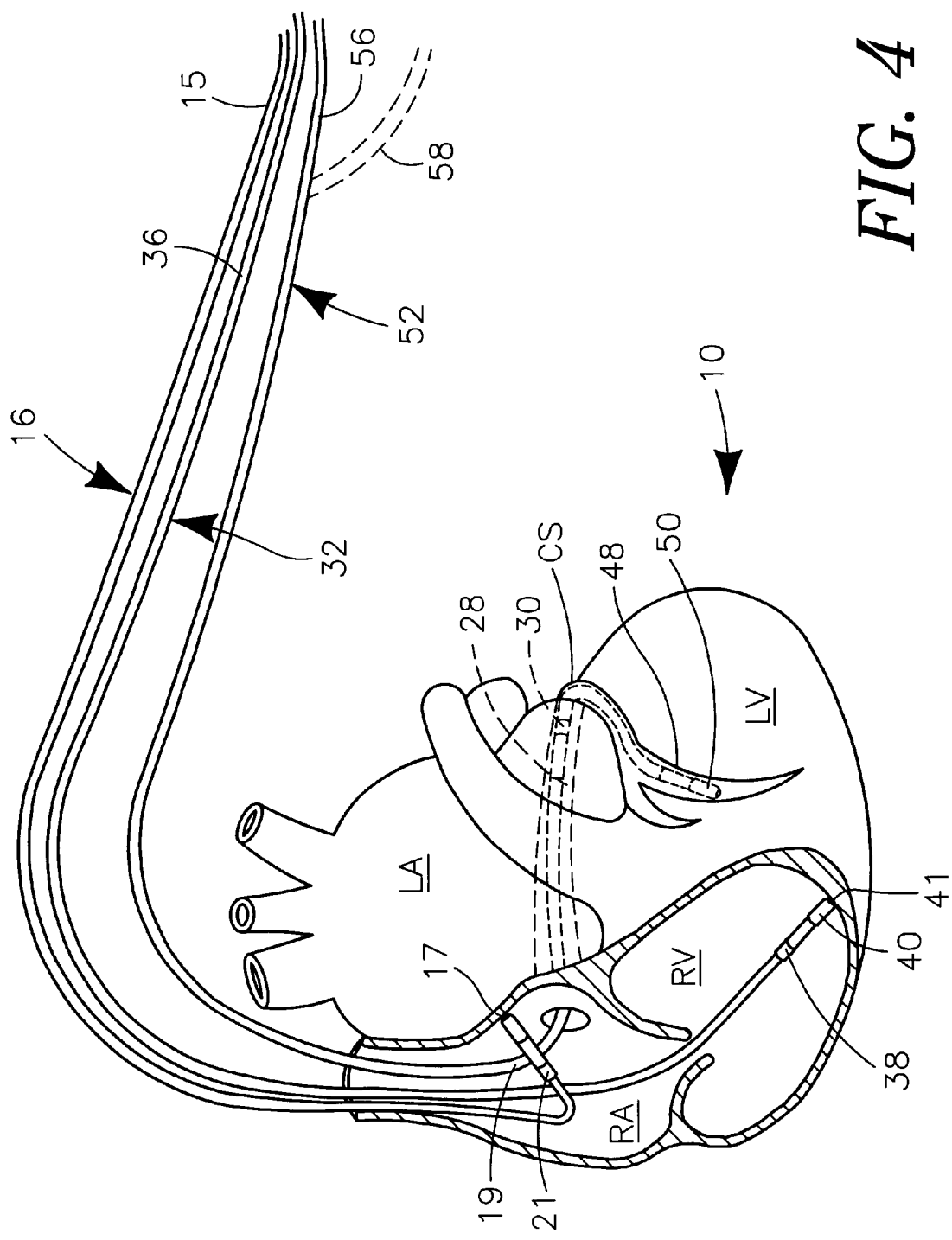
FIG. 4 is a diagram depicting a three or four channel, bi-atrial and/or bi-ventricular, implantable lead system with which the present invention may be employed.

Yet further, FIG. 4 is an illustrative, exemplary representation of a bi-atrial and/or bi-ventricular implantable lead system. RA lead 16 is coupled to a pair of electrically insulated conductors within lead body 15 that are connected with distal tip RA pace/sense electrode 19 and proximal ring RA pace/sense electrode 21. The distal end of the RA lead 15 is attached to the RA wall by a conventional attachment mechanism 17. Bipolar, endocardial RV lead 32 is passed through the vein into the RA chamber of the heart 10 and into the RV where its distal ring and tip RV pace/sense electrodes 38 and 40 are fixed in place in the apex by a conventional distal attachment mechanism 41. The RV lead 32 is coupled to a pair of electrically insulated conductors within lead body 36 and connected with distal tip RV pace/sense electrode 40 and proximal ring RV pace/sense electrode 38.

In this illustrative embodiment, a quadripolar, endocardial LV CS lead 52 is passed through a vein into the RA chamber of the heart 10, into the CS and then inferiorly in the great vein to extend the distal pair of LV CS pace/sense electrodes 48 and 50 alongside the LV chamber and leave the proximal pair of LA CS pace/sense electrodes 28 and 30 adjacent the LA. The LV CS lead 52 is formed with a four conductor lead body 56. The four electrically insulated lead conductors in LV CS lead body 56 are separately connected with one of the distal pair of LV CS pace/sense electrodes 48 and 50 and the proximal pair of LACS pace/sense electrodes 28 and 30.

As opposed to a quadripolar lead, the left atrial and left ventricular electrodes may be positioned in the heart chambers by a LV CS lead 52 that may include two bipolar lead bodies 56 and 58 (shown in dashed alternative configuration). As such, one lead body 56 may be coupled to LV CS pace/sense electrodes 48 and 50, and another lead body 58 may be coupled to LA CS pace/sense electrodes 28 and 30.

These illustrated bi-atrial and/or bi-ventricular pace/sense leads and electrode locations are merely exemplary of possible leads and electrode locations that can be employed in the practice of these embodiments of is the present invention. It will be understood that one or more of the other types of endocardial and epicardial leads and pace/sense electrodes located in or about the right and left chambers of the heart can be substituted for those illustrated in FIGS. 2–4 and described above. For example, the implantable leads shown in FIGS. 2–4 may also be unipolar bi-atrial and/or unipolar bi-ventricular leads, each having one conductor and a single electrode.

Figure 5:
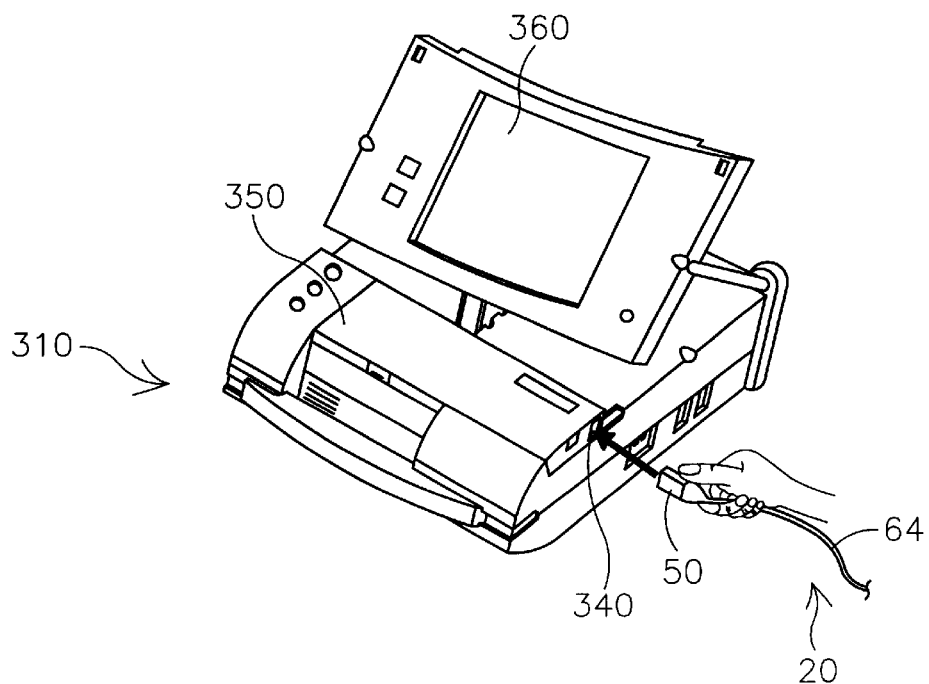
FIG. 5 is an illustration of an external medical device with which the present invention may be employed.

As previously mentioned, the present invention is directed to a patient safety cable apparatus 60 having an "in-parallel" configuration for use in connecting external medical devices 12 to implantable leads 16 (e.g., bi-atrial and/or bi-ventricular leads). FIG. 5 illustrates one embodiment of an external medical device 12 that may be connected to implantable lead systems 16 using the present invention. In FIG. 5, the external medical device is a programmer 310 that may include a keyboard 350, a display screen 360, and a receiving connector 340. Receiving connector 340 may include any suitable mating structure for connecting the programmer 310 to the patient safety cable 60 and, in particular, external lead connector assembly 50. Though a programmer is depicted, it should be understood that the external medical device 12 may also include an external pacemaker, analyzer, or any other external medical device that may be separately connected to one or more implantable leads 16 via cable 60. For example, any external medical device having a suitable mating structure for connecting to the external lead connector assembly 50 may be connected directly thereto, or, for example, the mating structure may require use of an adaptor to be so connected to the connector assembly 50.

As illustrated in FIG. 1, the patient safety cable apparatus 60 includes an external cable 62, an external lead connector assembly 50, and lead adaptors 90. The external cable 62 includes a first cable portion 64, a second cable portion 80, and a Y-connector portion 70. The first cable portion 64 is connected to the Y-connector portion 70 at a first end 66 thereof, while a second end 68 of the first cable portion 64 is connected to the external lead connector assembly 50. The external lead connector assembly 50 is preferably adapted to connect to or mate with a receiving connector 14 of external medical device 12.

Extending from the Y-connector 70 is the second cable portion 80. As illustrated in FIG. 1, the second cable portion 80 may include two or more cable lead elements 82 each preferably terminating at a lead adaptor 90. Each lead adapter 90 is configured to be coupled to one or more of the implantable leads 16. For example, for a bi-atrial lead configuration, each of two lead adaptors 90 would be individually coupled with one of the bi-atrial implantable leads 16.

The Y-connector portion 70, which is coupled with the first cable portion 64 at the first end 66, is configured to electrically connect the two or more cable lead elements 82 with one or more conductors of the first cable portion 64. Specifically, the Y-connector portion 70 includes at least one Y connection that is configured to electrically connect in parallel at least one pair of cable lead elements 82 (e.g., pair of lead elements that correspond to a pair of bi-atrial or a pair of bi-ventricular implantable leads) with one or more conductors of the first cable portion 64. In this in-parallel configuration, the cable 60 can be connected directly to at least one pair of bi-atrial or bi-ventricular implantable leads and to an external medical device 12 for use, for example, in pacing and/or sensing via the at least one pair of bi-atrial or bi-ventricular leads. For example, pacing pulses may be provided for the bi-atrial or bi-ventricular leads simultaneously via the in-parallel configuration employed via use of the Y-connection. Bi-atrial or bi-ventricular sensing may also be accomplished via the in-parallel configuration.

At the second end 68 of the first cable portion 64 is the external lead connector assembly 50 that is configured to connect to or mate with a receiving connector 14 of external medical device 12. The external lead connector assembly 50 can include any suitable mating structure known in the art for coupling or mating a cable with a device, e.g., RCA type plugs, banana plugs, threaded terminals. Preferably, the external lead connector assembly 50 is configured to prevent the patient safety cable apparatus 60 from becoming disconnected from the external medical device 12 during use. Such a configuration may preferably include a locking structure, or an engaging structure such as currently used on the 5436 safety cable available from Medtronic, Inc.

At an end of the patient safety cable apparatus 60 opposite from the external lead connector assembly 50 are lead adaptors 90. The lead adaptors 90 are configured to electrically couple or mate the cable lead elements 82 with the implantable leads 16. Any suitable connector structure known in the art may be utilized for lead adaptors 90, e.g., bare wire connections, male/female plug adaptors, wire locking terminals, etc.

Figure 6:
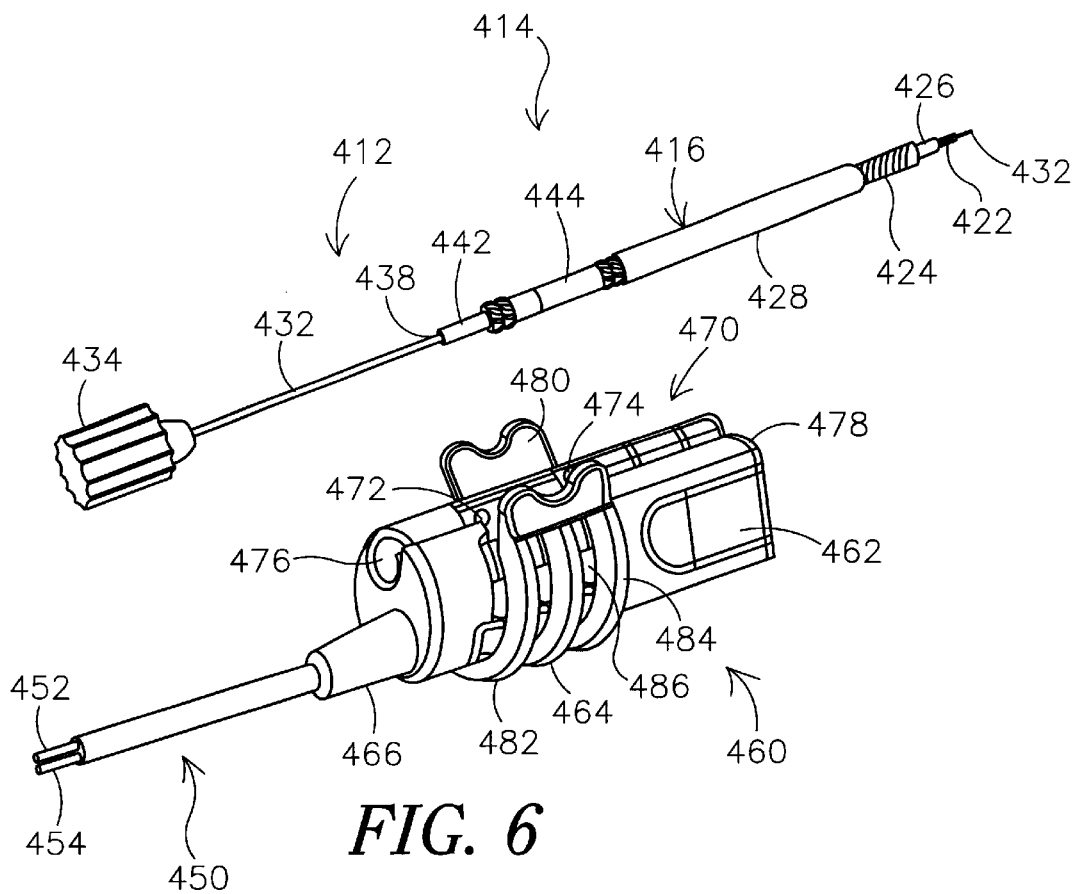
FIG. 6 is an exploded isometric partial view of the proximal end of an implantable lead oriented to be inserted into a connector receptacle of an adaptor connector assembly of one illustrative embodiment of a lead adaptor for use with the patient safety medical device cable apparatus shown generally in FIG. 1.

For example, FIG. 6 depicts one embodiment of a lead adaptor 410 as taught by Werner et al., U.S. Pat. No. 5,931,861, herein incorporated by reference. The proximal end of an implantable lead 414 is shown in part and includes an elongated implantable lead body 416. For purposes of illustration and convenience, the implantable lead 414 is depicted as a bipolar, in-line, permanent cardiac pacing lead employing co-axially wound, coiled wire, implantable lead conductors 422 and 424 separated apart by an insulating sheath 428. The outer implantable lead conductor 424 is coupled to a respective lead connector ring 444, and the inner implantable lead conductor 422 is coupled to a respective lead connector pin 442. A lumen is formed within the inner implantable lead conductor 422 for receiving a stiffening stylet wire 432 through a lumen end opening 438 in the lead connector pin 442. When the stylet wire 432 is received in the lumen, it extends proximally from the lumen end opening 438 so that the stylet knob 434 may be manipulated to rotate or axially extend or withdraw the stylet wire 432 with respect to the lead body lumen.

The lead adaptor 410 includes an external lead body 450 having at least one external electrical conductor therein extending between first and second external lead conductor ends thereof. Preferably, the external lead body 450 encases two electrically isolated external electrical conductors 452 and 454 of any known configuration electrically connected to contact terminals 472, 474 for making contact with the a conductors of the implantable lead 414.

An adaptor connector assembly 460 for receiving the lead connector end assembly 412 is formed at the end of the external lead body 450 and includes a housing 462 and a rotatable lock mechanism or clip 464. The housing 462 includes an elongated receptacle 470 that extends from the proximal and distal housing ends 476 and 478 and is shaped to conformably receive the lead connector end assembly 412 when laterally inserted therein through a receptacle slot 480. At least the lead connector ring 444 and pin 442 of the lead connector end assembly 412 are received in the elongated receptacle 470 between the proximal and distal housing ends 476, 478 so that they are not exposed.

Though one illustrative embodiment of a lead adaptor 92 is depicted in FIG. 6, lead adaptor 92 may include any suitable means known in the art for coupling one or more conductors to a lead, e.g., bipolar or unipolar implantable lead 16. For example, any structure that receives one or more conductors of an implantable lead 16 and locks such conductors in electrical connection with conductors of lead elements 82 of the second cable portion 80 may be used according to the present invention.

Various embodiments of the patient safety cable apparatus 60 in accordance with the present invention will now be described with reference to FIGS. 7–12. Once again, these embodiments are exemplary only and those of skill in the art will recognize that other embodiments are certainly possible without departing from the scope of the invention.

Figure 7:
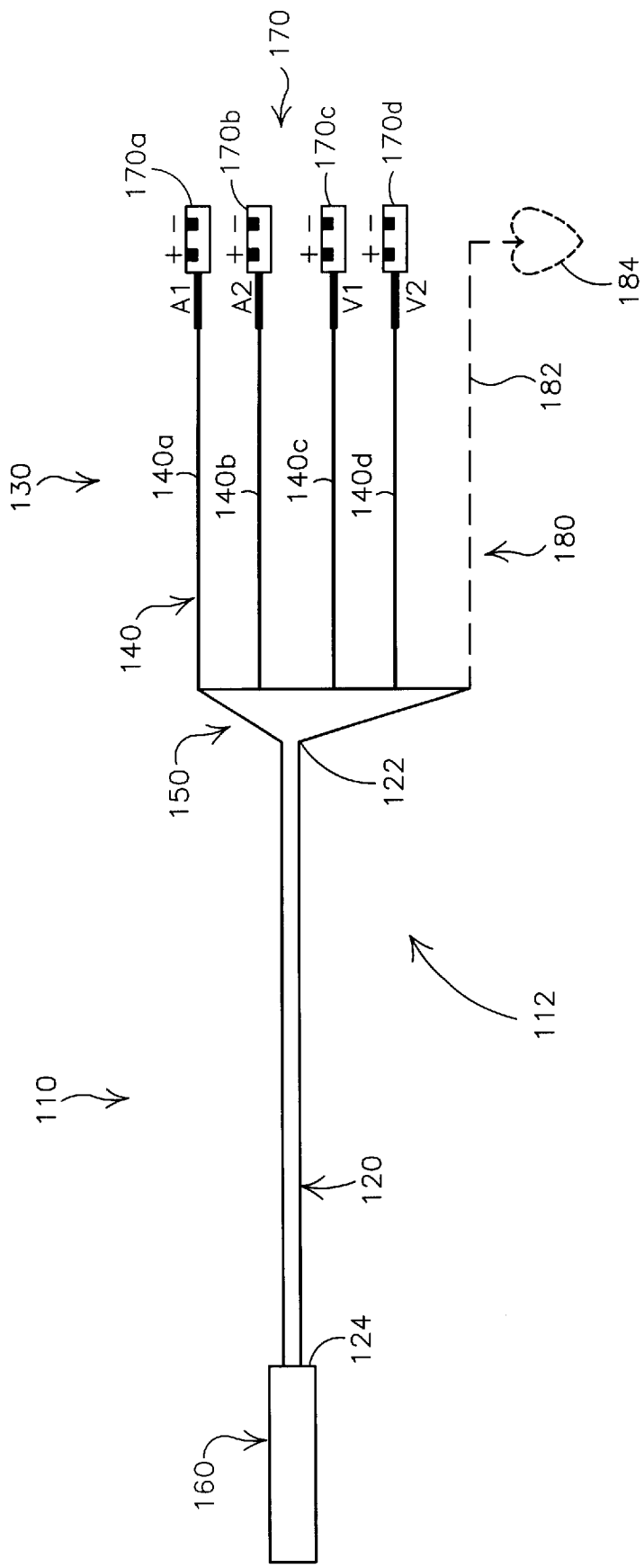
FIG. 7 is a diagram depicting an illustrative embodiment of the cable apparatus shown generally in FIG. 1, where the cable apparatus is a bi-atrial/bi-ventricular patient safety medical device cable apparatus.

FIG. 7 illustrates a patient safety cable 110 for use in connecting bi-ventricular and bi-atrial leads to an external medical device 12, e.g., unipolar or bipolar leads. As this figure illustrates, patient safety cable 110 includes a multi-conductor insulated external cable 112 which, in one embodiment, may include a first cable portion 120, a second cable portion 130, and a Y-connector portion 150. The first cable portion 120 connects to the Y-connector portion 150 at a first end 122 while a second end 124 of the first cable portion 120 terminates in an external lead connector assembly 160. The external lead connector assembly 160 is preferably adapted to connect to a receiving connector (e.g., connector 14 of the external medical device 12 of FIG. 1), as described with reference to FIG. 1.

Extending from the Y-connector portion 150 is the second cable portion 130. The second cable portion 130 may include two or more cable lead elements 140a, 140b, 140c, and 140d, (generically or collectively referred to hereinafter as cable lead elements 140). The end of the second cable portion 130, i.e., the end of each lead element 140, preferably terminates at respective lead adaptors 170a, 170b, 170c, and 170d, (generically or collectively referred to hereinafter as cable lead adaptors 170). Cable lead elements 140 correspond to a pair of bi-atrial implantable leads and a pair of bi-ventricular implantable leads (e.g., implantable leads 16 as depicted in FIG. 1). The two or more cable lead elements 140 may be coupled with bipolar implantable leads using the lead adaptors 170 by connection of the conductor of the implantable leads to respective +/− terminals of each lead adaptor. It will be recognized that a lead adaptor having more terminals may be used to accommodate implantable leads having more than two conductors such as a quadripolar lead.

Also depicted in FIG. 7 is an indifferent electrode 180 including an indifferent electrode lead element 182 and a body coupler 184. The indifferent electrode 180 may be coupled with one or more conductors of the multi-conductor insulated external cable 112 for use during unipolar pacing as further described below.

The Y-connector portion 150 allows pairs of bi-atrial and bi-ventricular implantable leads to be connected in-parallel when bi-atrial implantable leads are connected to RA/LA lead elements 140a–140b via lead adaptor 170a–170b and when bi-ventricular implantable leads are connected to RV/LV lead elements 140c–140d via lead adaptors 170c–170d. In other words, two channels, i.e., atrial and ventricular, are established by the in-parallel configuration. For example, such a cable may be connected directly to the MEDTRONIC® 8090 Analyzer or to any external pacemaker with a safety port or other mating structure compatible with external lead connector assembly 160 (e.g., safety plug 160). Both dual unipolar and dual bipolar application functional connection configurations are possible for each channel, either atrial or ventricular, as further described below with reference to FIGS. 8 and 9.

Figure 8:
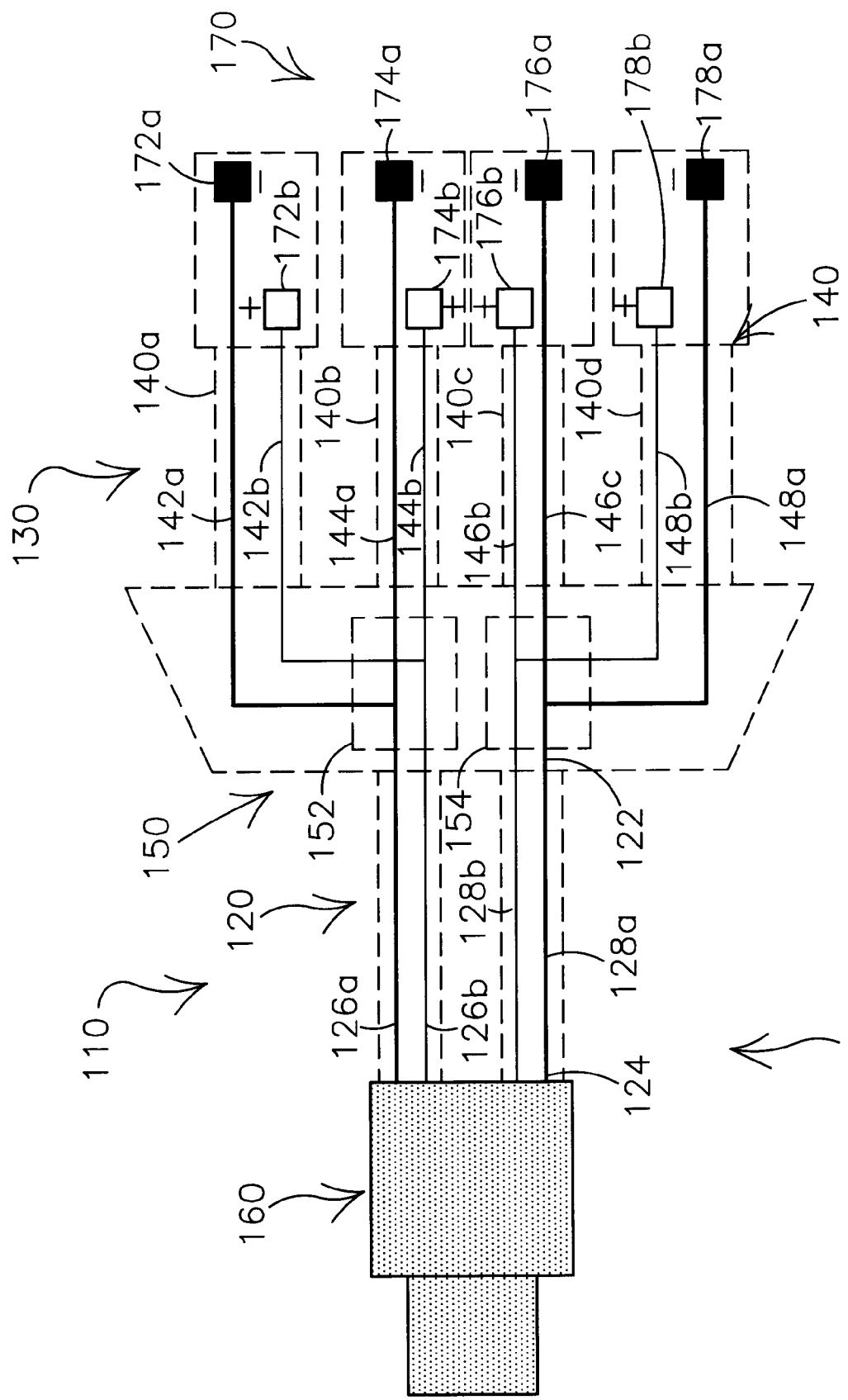
FIG. 8 is a schematic diagram depicting one illustrative embodiment of the bi-atrial/bi-ventricular patient safety medical device cable apparatus of FIG. 7.

FIG. 8 is a schematic diagram of one embodiment of the patient safety cable 110 configured for bipolar bi-atrial and bi-ventricular lead connection. Patient safety cable 110 includes the external cable 112, the external lead connector assembly 160, and the lead adaptors 170. The external cable 112 includes first cable portion 120, second cable portion 130, and Y-connector portion 150.

The first cable portion 120 includes conductors 126a and 128a held at a negative potential when the cable 110 is being used and connected to the external medical device 12 (hereafter negative conductors), and positive conductors 126b and 128b held at a positive potential when cable 110 is being used in such a manner (hereinafter positive conductors). Each of the conductors within the first cable portion 120 may include any suitable material for electrical conduction, e.g., copper, aluminum, and be insulated appropriately from one another. Further, it will be recognized that leads of opposite polarity may be used.

Extending from the Y-connector portion 150 is the second cable portion 130. The second cable portion 130 includes cable lead elements 140, including RA lead element 140a, LA lead element 140b, RV lead element 140c, and LV lead element 140d. Each individual lead element includes two conductors corresponding to, for example, conductors of a bipolar implantable lead. For example, RA lead element 140a may include negative lead element conductor 142a and positive lead element conductor 142b. Further, LA lead element 140b includes negative lead element conductor 144a and positive lead element conductor 144b; RV lead element 140c includes negative lead element conductor 146a and positive lead element conductor 146b; and LV lead element 140d includes negative lead element conductor 148a and positive lead element conductor 148b.

The end of the second cable portion 130, i.e., the end of each lead element 140, preferably terminates at respective lead adaptors 170.

Within each lead adaptor 170 are two terminals for electrical connection to bipolar leads having a potential difference therebetween when the patient safety cable 110 is connected to the external medical device 12. For example, RA lead adaptor 170a includes negative terminal 172a and positive terminal 172b. The other terminals of respective lead adaptors include terminals 174a–b, 176a–b, and 178a–b.

Included within the Y connector portion 150 of the external cable 112 is a first Y connection 152 and a second Y connection 154. The first Y connection 152 electrically connects negative lead element conductors 142a and 144a together with the negative conductor 126a of the first cable portion 120 in an in-parallel configuration. Also, the first Y connection 152 electrically connects the positive lead element conductors 142b and 144b together with the positive conductor 126b of the first cable portion 120, also in an in-parallel configuration. Similarly, the second Y connection 154 connects in a parallel configuration the negative cable lead elements 144a and 146a with the negative conductor 128a of the first cable portion, and 144b and 146b positive cable lead elements with the positive conductor 128b of the first cable portion.

The conductors 126a and 126b and the conductors 128a and 128b are terminated in external connector assembly 160. For example, such termination may be in the form of plugs to be received by a receptacle of the external medical device 12 or any other termination techniques such as that used in the 5436 cable previously mentioned herein. With the lead adaptors 170 connected to implantable LA/RA/LWRV bipolar leads via terminals 172a–b, 174a–b, 176a–b, and 178a–b respectively, appropriate signals can be transmitted to the electrodes of such bipolar leads and received by the external medical device 12 using such leads.

Figure 9:
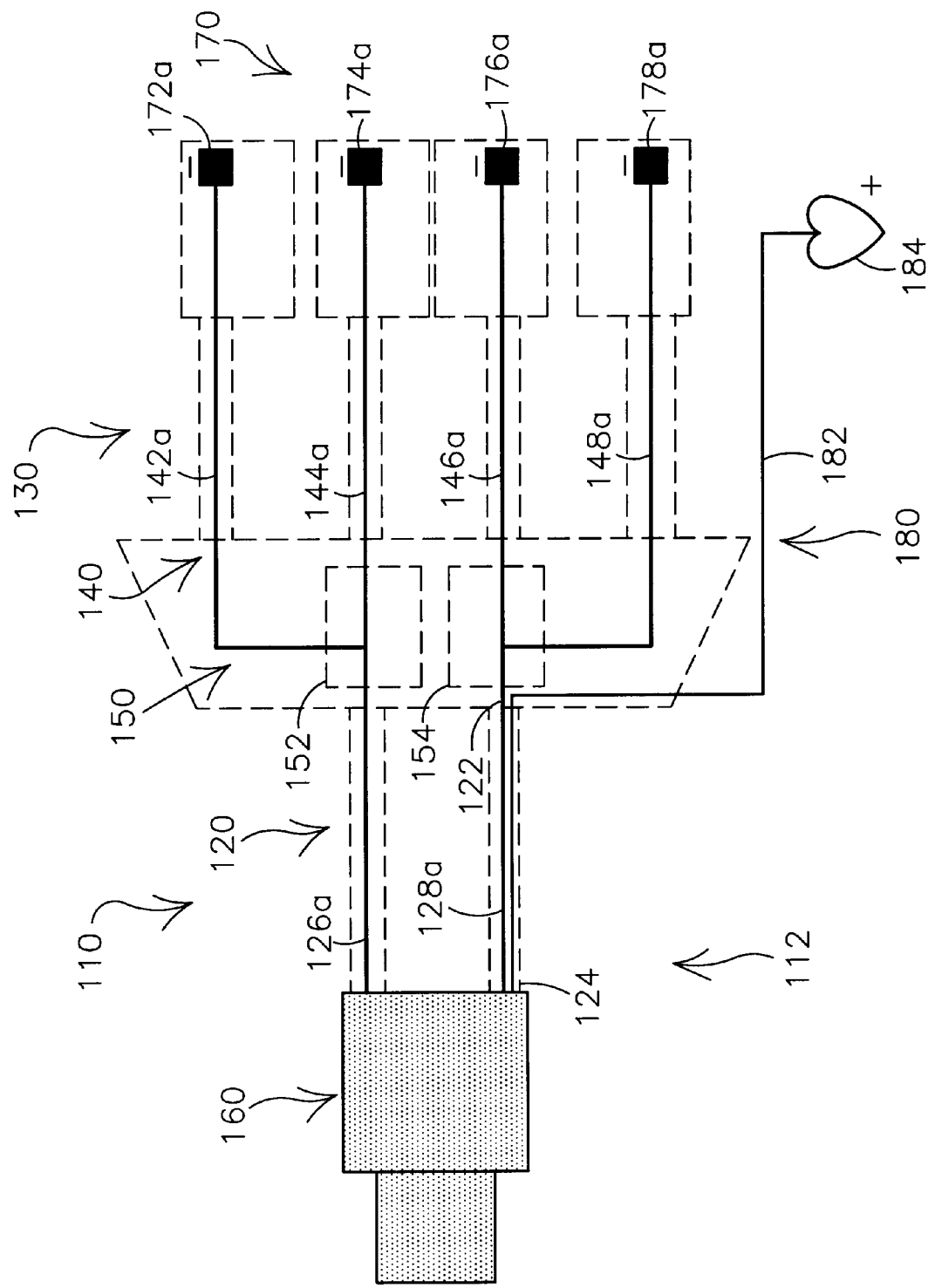
FIG. 9 is a schematic diagram of another illustrative embodiment of the bi-atrial/bi-ventricular patient safety medical device cable apparatus of FIG. 7.

In FIG. 9, a schematic of another embodiment of the cable 110 of the present invention is depicted. FIG. 9 illustrates a safety cable 110 for unipolar, bi-atrial and bi-ventricular lead connection. In this embodiment, only the negative portion (e.g., negative conductors, negative terminals, etc.) of the cable 110 shown in FIG. 8 are used in conjunction with indifferent electrode 180. The indifferent electrode 180 is used for one return path. The conductors 126a and 128a are terminated in external connector assembly 160. Further, the indifferent electrode 180 is terminated in external connector assembly 160 by any suitable means known in the art, e.g., plug termination, socket termination, etc. With the lead adaptors 170a–170d connected to implantable unipolar LNRALV/RV leads via terminals 172a, 174a, 176a, and 178a, respectively, appropriate signals can be transmitted to electrodes of such unipolar leads and received by the external medical device 12 using such unipolar leads.

Figure 10:
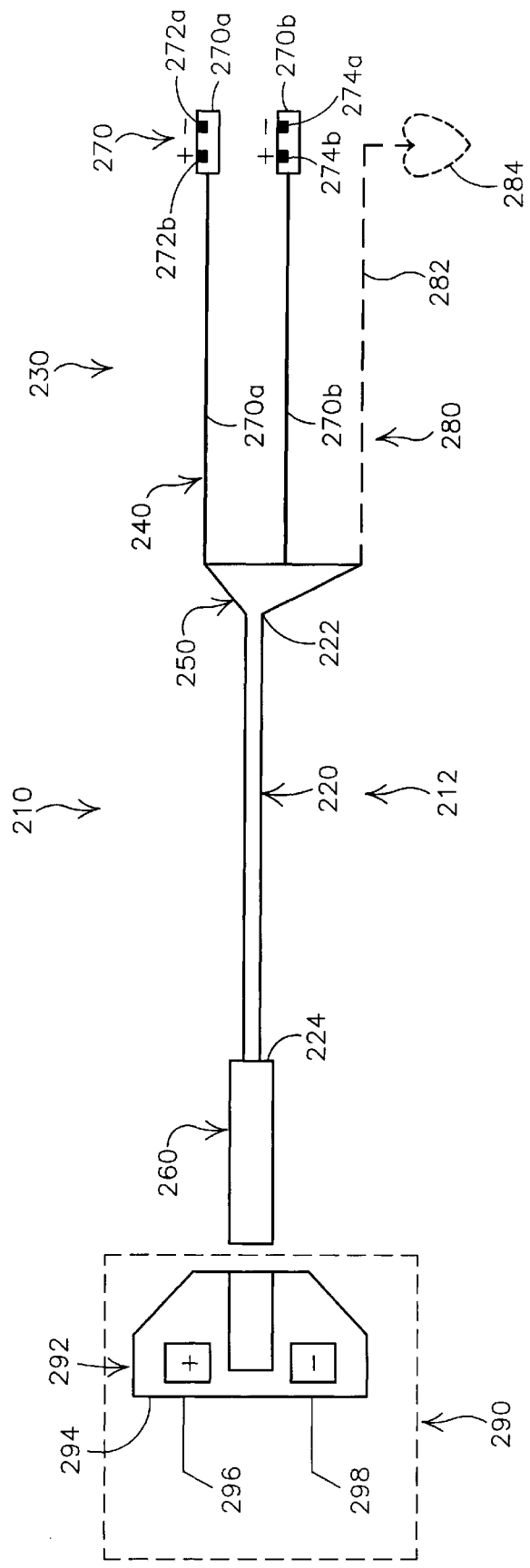
FIG. 10 is a diagram depicting another illustrative embodiment of the cable apparatus shown generally in FIG. 1, where the cable apparatus is a bi-atrial or a bi-ventricular patient safety medical device cable apparatus.

FIG. 10 is illustrative of an alternative embodiment of the patient safety cable 60 of FIG. 1 according to the present invention. In FIG. 10, patient safety cable 210 is configured for either bi-atrial or bi-ventricular lead connection, e.g., unipolar or bipolar lead connection. As this FIG. 10 illustrates, patient safety cable 210 includes a multi-conductor insulated external cable 212, which includes a first cable portion 220, a second cable portion 230, and a Y-connector portion 250. The first cable portion 220 connects to the Y-connector portion 250 at a first end 222 while a second end 224 of the first cable portion 220 terminates in external lead connector assembly 260. The external lead connector assembly 260 is preferably adapted to connect to a receiving connector (e.g., connector 14 of the external medical device 12 of FIG. 1.

Extending from the Y-connector portion 250 is the second cable portion 230. The second cable portion 230 includes cable lead elements 240 including a first cable lead element 240a and a second cable lead element 240b. The end of the second cable portion 230, i.e., the end of cable lead elements 240, preferably terminates at respective lead adaptors 270. Cable lead element 240a terminates at lead adaptor 270a, and cable lead element 240b terminates at lead adaptor 270b. Preferably, the cable lead elements 240 correspond to a pair of bi-atrial implantable leads or a pair of bi-ventricular implantable leads (e.g., implantable unipolar or bipolar leads 16 as depicted in FIG. 1). The cable lead elements 240 may be coupled to implantable leads using the lead adaptors 270, e.g., lead adaptor 410 of FIG. 6, via +/− contact terminals.

At the second end 224 of the first cable portion 220 is the external lead connector assembly 260, which is configured to connect to or mate with a receiving connector 14 of external medical device 12. The external lead connector assembly 260 can include any suitable mating structure known in the art for coupling or mating a cable with a device, e.g., RCA type plugs, banana plugs, threaded terminals, sockets. Preferably, the external lead connector assembly 260 is configured to prevent the patient safety cable apparatus 210 from becoming disconnected from the external medical device 12 during use. Such a configuration may include a locking structure, or an engaging structure such as currently used on the 5436 safety cable available from Medtronic, Inc.

Alternatively, external lead assembly 260 may be coupled to an adaptor 290 for attaching the patient safety cable 210 with an external medical device (i.e., external medical device 12 of FIG. 1). In FIG. 10, the adaptor 290 is depicted as adaptor 292 including adaptor body 294, positive adaptor pin 296, and negative adaptor pin 298. For example, the adaptor 290 may be used to connect the patient safety cable 210 to an AAI or VVI external pacemaker with a safety port, e.g., a MEDTRONIC® 5101 Adaptor would enable the patient safety cable 210 to be connected to certain external AAINVI/DDD Medtronic pacemakers that are known in the art. Both unipolar and bipolar configurations are possible using adaptor 290.

Also depicted in FIG. 10 is an indifferent electrode 280 including an indifferent electrode lead element 282 and a body coupler 284. The indifferent electrode 280 may be coupled to a conductor of the multi-conductor insulated external cable 212 and terminated in the external lead assembly connector 260 for use in a unipolar configuration as further described below.

Figure 11:
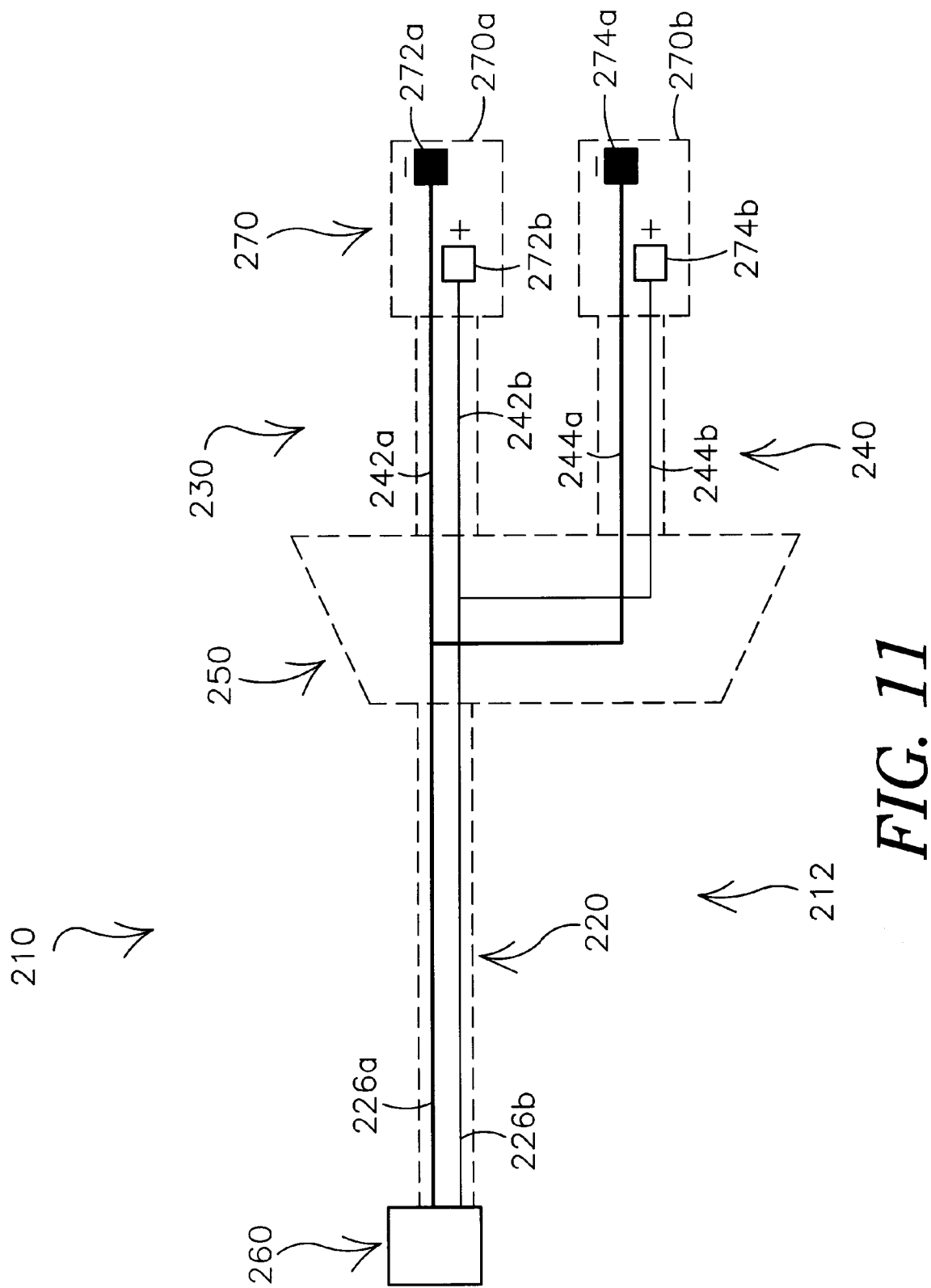
FIG. 11 is a schematic diagram of one illustrative embodiment of the bi-atrial or bi-ventricular patient safety medical device cable apparatus of FIG. 10.

FIG. 11 illustrates a schematic diagram of the patient safety cable 210 of FIG. 10 in a bipolar lead connection configuration. In FIG. 11, patient safety cable 210 includes the multi-conductor insulated external cable 212, which includes the first cable portion 220, the second cable portion 230, and the Y-connector portion 250. The end of the second cable portion 230, i.e., the end of cable lead elements 240, preferably terminates at lead adaptors 270. Cable lead element 240a terminates at lead adaptor 270a, and cable lead element 240b terminates at lead adaptor 270b. First lead adaptor 270a, which terminates the first cable lead element 240a, includes a negative terminal 272a and a positive terminal 272b. Similarly, second lead adaptor 270b, which terminates the second pace/sense lead element 240b, includes a negative terminal 274a and a positive terminal 274b. The cable lead elements 240 preferably correspond to a pair of bipolar bi-atrial implantable leads or a pair of bipolar bi-ventricular implantable leads (e.g., implantable leads 16 as depicted in FIG. 1). The cable lead elements 240 may be coupled with bipolar implantable leads using lead adaptors 270 (e.g., lead adaptor 410 of FIG. 6). For example, a first bipolar bi-atrial lead may be connected to terminals 272a and 272b of the lead adaptor 270a, and a second bipolar bi-atrial lead may be connected to terminals 274a and 274b of the lead adaptor 270b.

Within the first cable lead element 240a is a negative lead conductor 242a and a positive lead conductor 242b. Similarly, the second cable lead element 240b includes a negative lead conductor 244a and a positive lead conductor 244b. Further, first cable portion 220 includes negative and positive conductors 226a and 226b, respectively.

The Y-connector portion 250 includes a Y connection that electrically connects in parallel the negative conductor 242a of the first cable lead element 240a and the negative conductor 244a of the second cable lead element 240b to the negative conductor 226a of the first cable portion 220. Similarly, the Y connection electrically connects in parallel the positive conductor 242b of the first cable lead element 240a and the positive conductor 244b the cable lead element 244 to the positive conductor 226b of the first cable portion 220 of the external cable 212.

Figure 12:
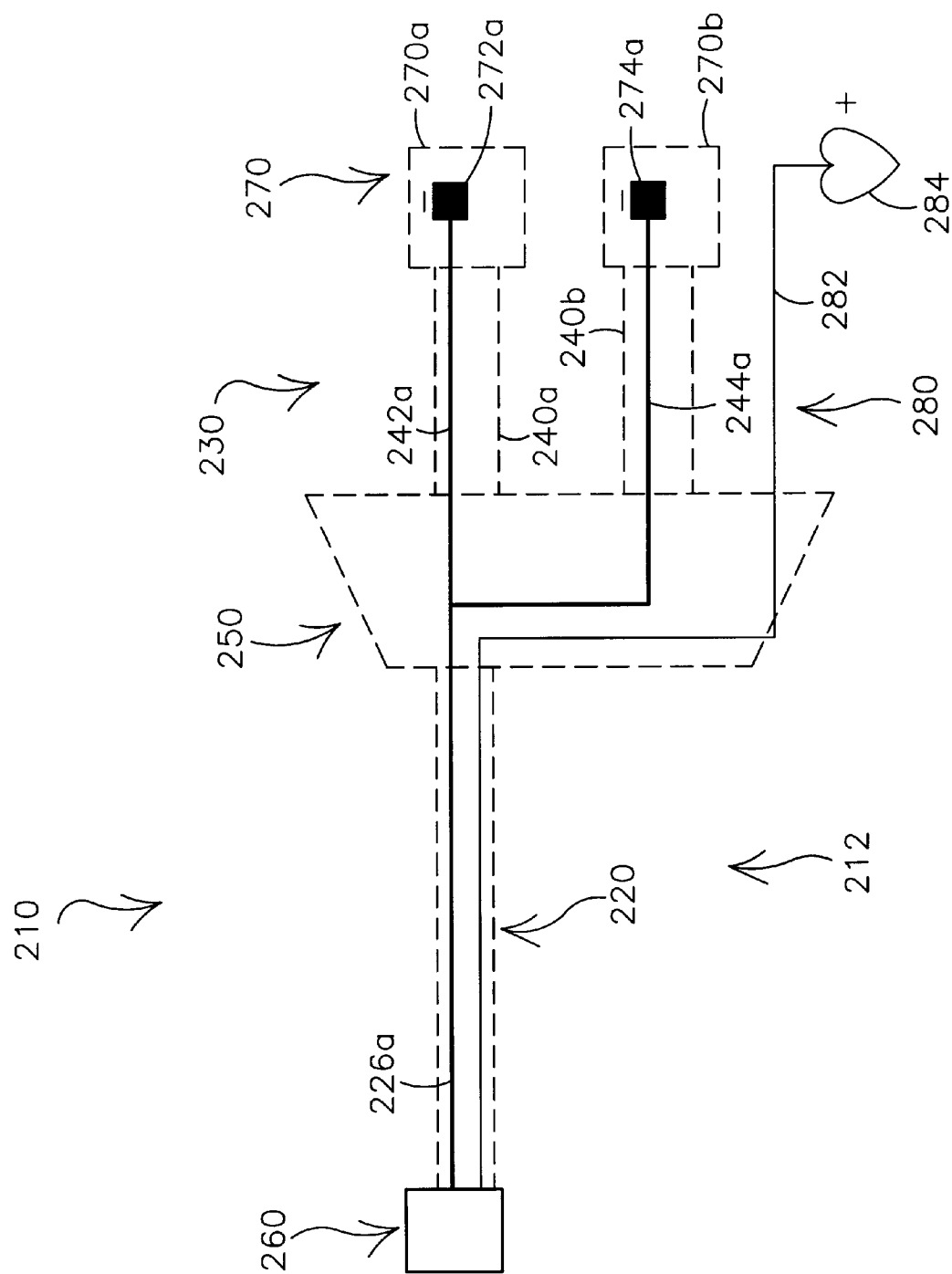
FIG. 12 is a schematic diagram of another illustrative embodiment of the bi-atrial or bi-ventricular patient safety medical device cable apparatus of FIG. 10.

The conductors 226a and 226b are terminated in external connector assembly 260. For example, the termination may be in the form of plugs to be received by a receptacle of the external medical device 12. With the lead adaptors 270a and 270b connected to either implantable bipolar RA/LA leads or RV/LV leads respectively, appropriate signals can be transmitted to electrodes of such bipolar leads and received by the external medical device 12 using such leads. FIG. 12 depicts another embodiment of the present invention where the patient safety cable 210 is connected in a unipolar configuration. In this embodiment, only the negative portion (e.g., negative conductors, negative terminals, etc.) of the cable 210 of FIG. 11 are used in conjunction with the indifferent electrode 280. Patient safety cable 210 includes the multi-conductor insulated external cable 212 that includes the first cable portion 220, the second cable portion 230, and the Y-connector portion 250.

Further, the first cable portion includes the negative conductor 226 and the indifferent electrode 280. In a unipolar configuration, the negative conductors are used with the positive indifferent electrode to provide appropriate unipolar connection of an external medical device 12 to a pair of bi-atrial or bi-ventricular leads.

Preferably, the cable lead elements 240a–b correspond to a pair of is unipolar bi-atrial implantable leads or a pair of unipolar bi-ventricular implantable leads (e.g., implantable leads 16 as depicted in FIG. 1). The cable lead elements 240 may be coupled with the unipolar implantable leads using lead adaptors 270, e.g., the negative terminals 272a and 274a of the lead adaptors 270a and 270b, respectively.

The conductor 226a is terminated in external connector assembly 260. For example, this termination may be in the form of plugs to be received by a receptacle of the external medical device 12. With the lead adaptors 270a and 270b connected to implantable unipolar RA/LA leads or unipolar RV/LV leads respectively, appropriate signals can be transmitted to the electrodes of such unipolar leads and received by the external medical device 12 using such leads.

One skilled in the art will recognize from the description herein that bipolar leads or unipolar leads may be connected using the cable apparatus shown in FIGS. 7 and 10. However, such cable apparatus may be provided that only connects bipolar or only connects unipolar leads to the external medical device. For example, cables following the schematics of FIGS. 8 and 11 for bipolar leads and FIGS. 9 and 12 for unipolar leads may be provided.

With reference to FIG. 1, a method for electrically connecting one or more implantable leads 16 to an external medical device 12 is herein described. The patient safety medical device cable apparatus 60 is provided including an external cable 62, an external lead connector assembly 50, and two or more lead adaptors 90. Implantable leads 16 may include a pair of bi-atrial implantable leads and/or a pair of bi-ventricular implantable leads. Further, said leads may be bipolar or unipolar. The patient safety medical device cable apparatus 60 is employed by attaching at least one of the two or more lead adaptors 90 to at least one pair of bi-atrial implantable leads and/or bi-ventricular implantable leads 16. The external lead connector assembly 50 may be attached to an external medical device by coupling the external lead connector assembly 50 with the receiving connector 14 of the external medical device. In such a manner, an in-parallel configuration of the bi-atrial and/or bi-ventricular leads is attained such that appropriate signaling between the external medical device 12 and leads 16 can be performed. For bipolar leads, both electrodes thereof are coupled through terminals of the lead adaptors as previously described herein.

In the alternative unipolar configuration, electrodes of the unipolar leads are coupled through terminals of the lead adaptors. Further, an indifferent electrode 180 including an indifferent electrode lead element 182 and a body coupler 184 are coupled to the patient to provide a return path.

The complete disclosure of the patents, patent documents, and publications cited in the Background, Detailed Description of the Embodiments and elsewhere herein are incorporated by reference in their entirety as if each were individually incorporated.

The preceding specific embodiments are illustrative of the practice of the invention. It is to be understood, therefore, that other expedients known to those skilled in the art or disclosed herein may be employed without departing from the invention or the scope of the appended claims. For example, the present invention is not limited to the use of patient safety cables for bi-atrial and/or bi-ventricular functions in connection with an analyzer or external pacemaker, but may be used with any appropriate medical device. The present invention further includes within its scope methods of making and using apparatus described herein above.

What is claimed is:

1. A patient safety medical device cable apparatus comprising:
    a multi-conductor insulated external cable, the external cable comprising:
        a first cable portion having a first end and a second end, wherein the first cable portion comprises one or more conductors;
        a second cable portion comprising at least one pair of external cable lead elements, wherein each of the at least one pair of external cable lead elements corresponds to one of a pair of bi-atrial implantable leads and a pair of bi-ventricular implantable leads;
        a Y-connector portion connected to the first end of the first cable portion, wherein the Y-connector portion comprises at least one Y connection electrically connecting the at least one pair of external cable lead elements with one or more conductors of the first cable portion;
    an external lead connector assembly terminating the second end of the first cable portion and configured to be electrically connected to an external medical device; and
    two or more lead adaptors, wherein each lead adaptor is configured for electrical connection to an implantable lead, and further wherein each of the external cable lead elements of the at least one pair of external cable lead elements is terminated by one of the two or more lead adaptors.

2. The apparatus according claim 1, wherein the apparatus further comprises an indifferent electrode, lead element associated with at least the first cable portion and configured to be electrically connected with a patient, and further wherein the external lead connector assembly terminates the indifferent electrode lead element.

3. The apparatus according to claim 1, wherein the second cable portion comprises a single pair of external cable lead elements, and further wherein the single pair of external cable lead elements corresponds to a single pair of bi-atrial implantable leads.

4. The apparatus according to claim 1, wherein the second cable portion comprises a single pair of external cable lead elements, and further wherein the single pair of external cable lead elements corresponds to a single pair of bi-ventricular implantable leads.

5. The apparatus according to claim 1, wherein the second cable portion comprises two pairs of external cable lead elements, wherein the two pairs of external cable lead elements correspond to a single pair of bi-atrial implantable leads and a single pair of bi-ventricular implantable leads.

6. The apparatus of claim 1, wherein the external medical device comprises an external pacemaker.

7. The apparatus of claim 1, wherein the external medical device comprises a programmer.

8. The apparatus of claim 1, wherein the external medical device comprises an analyzer.

9. A patient safety medical device cable apparatus comprising:
    a multi-conductor insulated external cable, the external cable comprising:
        a first cable portion having a first end and a second end, wherein the first cable portion comprises one or more conductors;
        a second cable portion comprising a first external lead element and a second external lead element, wherein the first external lead element and the second external lead element correspond to a first bi-atrial implantable lead and a second bi-atrial implantable lead, respectively;

a Y-connector portion connected to the first end of the first cable portion, wherein the Y-connector portion comprises a Y connection electrically connecting the first external lead element and the second external lead element with one or more conductors of the first cable portion;

an external lead connector assembly terminating the second end of the first cable portion and configured to be electrically connected to an external medical device; and a first lead adaptor and a second lead adaptor, wherein each lead adaptor is configured for electrical connection to an implantable lead, and further wherein the first external lead element is terminated by the first lead adaptor and the second external lead element is terminated by the second lead adaptor.

10. The apparatus according to claim 9, wherein the apparatus further comprises an indifferent electrode lead element associated with at least the first cable portion and configured to be electrically connected with a patient and terminated by the external lead connector assembly, wherein the first external lead element comprises at least one conductor of a first polarity when the external lead connector assembly is electrically connected to the external medical device, wherein the second external lead element comprises at least one conductor of a first polarity when the external lead connector assembly is electrically connected to the external medical device, and further wherein the indifferent electrode lead element comprises a conductor of a second polarity when the external lead connector assembly is electrically connected to the external medical device.

11. The apparatus according to claim 9, wherein the first external lead element and the second external lead element comprise at least one conductor of a first polarity when the external lead connector assembly is electrically connected to the external medical device and at least one conductor of a second polarity when the external lead connector assembly is electrically connected to the external medical device, wherein the Y connection connects the at least one conductor of a first polarity of the first external lead element and second external lead element to at least one conductor of a first polarity of the first cable portion, and further wherein the Y connection connects the at least one conductor of a second polarity of the first external lead element and second external lead element to at least one conductor of a second polarity of the first cable portion.

12. The apparatus according to claim 9, wherein the external medical device is at least one of an external pacemaker, a programmer, and an analyzer.

13. A patient safety medical device cable apparatus comprising:

a multi-conductor insulated external cable, the external cable comprising:

a first cable portion having a first end and a second end, wherein the first cable portion comprises one or more conductors;

a second cable portion comprising a first external lead element and a second external lead element, wherein the first external lead element and the second external lead element correspond to a first bi-ventricular implantable lead and a second bi-ventricular implantable lead, respectively;

a Y-connector portion connected to the first end of the first cable portion, wherein the Y-connector portion comprises a Y connection electrically connecting the first external lead element and the second external lead element with one or more conductors of the first cable portion;

an external lead connector assembly terminating the second end of the first cable portion and configured to be electrically connected to an external medical device; and a first lead adaptor and a second lead adaptor, wherein each lead adaptor is configured for electrical connection to an implantable lead, and further wherein the first external lead element is terminated by the first lead adaptor and the second external lead element is terminated by the second lead adaptor.

14. The apparatus according to claim 13, wherein the apparatus further comprises an indifferent electrode lead element associated with at least the first cable portion and configured to be electrically connected with a patient and terminated by the external lead connector assembly, wherein the first external lead element comprises at least one conductor of a first polarity when the external lead connector assembly is electrically connected to the external medical device, wherein the second external lead element comprises at least one conductor of a first polarity when the external lead connector assembly is electrically connected to the external medical device, and further wherein the indifferent electrode lead element comprises a conductor of a second polarity when the external lead connector assembly is electrically connected to the external medical device.

15. The apparatus according to claim 13, wherein the first external lead element and the second external lead element comprise at least one conductor of a first polarity when the external lead connector assembly is electrically connected to the external medical device and at least one conductor of a second polarity when the external lead connector assembly is electrically connected to the external medical device, wherein the Y connection connects the at least one conductor of a first polarity of the first external lead element and second external lead element to at least one conductor of a first polarity of the first cable portion, and further wherein the Y connection connects the at least one conductor of a second polarity of the first external lead element and second external lead element to at least one conductor of a second polarity of the first cable portion.

16. The apparatus according to claim 13, wherein the external medical device is at least one of an external pacemaker, a programmer, and an analyzer.

17. A patient safety medical device cable apparatus comprising:

a multi-conductor insulated external cable, the external cable comprising:

a first cable portion having a first end and a second end, wherein the first cable portion comprises one or more conductors;

a second cable portion comprising a first pair of external cable lead elements and a second pair of external cable lead elements, wherein the first pair of external cable lead elements corresponds to a pair of bi-atrial implantable leads, and further wherein the second pair of external cable lead elements corresponds to a pair of bi-ventricular implantable leads;

a Y-connector portion connected to the first end of the first cable portion, wherein the Y-connector portion comprises a first Y connection and a second Y connection, wherein the first Y connection electrically connects the first pair of external cable lead elements with one or more conductors of the first cable portion, and further wherein the second Y connection electrically connects the second pair of external cable lead elements with one or more conductors of the first cable portion;

an external lead connector assembly terminating the second end of the first cable portion and configured to be electrically connected to an external medical device; and a plurality of lead adaptors, wherein each lead adaptor is configured for electrical connection to an implantable lead, and further wherein each of the external cable lead elements of the first pair of external cable lead elements and each of the second pair of external cable lead elements is terminated by one of the plurality of lead adaptors.

18. The apparatus according to claim 17, wherein the apparatus further comprises an indifferent electrode lead element associated with at least the first cable portion and configured to be electrically connected with a patient and terminated by the external lead connector assembly, wherein each of the external cable lead elements of the first pair of external cable lead elements and the second pair of external cable lead elements comprises at least one conductor of a first polarity when the external lead connector assembly is electrically connected to the external medical device, and further wherein the indifferent electrode lead element comprises a conductor of a second polarity when the external lead connector assembly is electrically connected to the external medical device.

19. The apparatus according to claim 17, wherein each of the external cable lead elements of the first pair of external cable lead elements and the second pair of external cable lead elements comprises at least one conductor of a first polarity when the external lead connector assembly is electrically connected to the external medical device and at least one conductor of a second polarity when the external lead connector assembly is electrically connected to the external medical device, wherein the first Y connection connects the at least one conductor of a first polarity of the first pair of external cable lead elements to at least one conductor of a first polarity of the first cable portion, wherein the first Y connection connects the at least one conductor of a second polarity of the first pair of external cable lead elements to at least one conductor of a second polarity of the first cable portion, wherein the second Y connection connects the at least one conductor of a first polarity of the second pair of external cable lead elements to at least one conductor of a first polarity of the first cable portion, and further wherein the second Y connection connects the at least one conductor of a second polarity of the second pair of external cable lead elements to at least one conductor of a second polarity of the first cable portion.

20. The apparatus according to claim 17, wherein at least one lead adaptor of the plurality lead adaptors is configured for electrical connection to a quadripolar implantable lead.

21. The apparatus according to claim 17, wherein the external medical device is at least one of an external pacemaker, a programmer, and an analyzer.

22. A method for electrically connecting one or more implantable leads to an external medical device, the method comprising:

providing a patient safety medical device cable apparatus comprising:

a multi-conductor insulated external cable, the external cable comprising:

a first cable portion having a first end and a second end, wherein the first cable portion comprises one or more conductors;

a second cable portion comprising at least one pair of external cable lead elements, wherein each of the at least one pair of external cable lead elements corresponds to one of a pair of bi-atrial implantable leads and a pair of bi-ventricular implantable leads;

a Y-connector portion connected to the first end of the first cable portion, wherein the Y-connector portion comprises at least one Y connection electrically connecting the at least one pair of external cable lead elements with one or more conductors of the first cable portion;

an external lead connector assembly terminating the second end of the first cable portion and configured to be electrically connected to an external medical device; and two or more lead adaptors, wherein each lead adaptor is configured for electrical connection to an implantable lead, and further wherein each of the external cable lead elements of the at least one pair of external cable lead elements is terminated by one of the two or more lead adaptors;

electrically coupling at least one of the two or more lead adaptors to at least one of the implantable leads of the pair of bi-atrial implantable leads and the pair of bi-ventricular implantable leads; and attaching the external lead connector assembly to the external medical device.

23. The method according to claim 22, wherein the patient safety medical device cable apparatus further comprises an indifferent electrode lead element terminated by the external lead connector assembly, and further wherein the method comprises connecting the indifferent electrode lead element with a patient.

24. The method according to claim 22, wherein the second cable portion of the patient safety medical device cable apparatus comprises a single pair of external cable lead elements, wherein the single pair of external cable lead elements corresponds to a single pair of bi-atrial implantable leads, and further wherein electrically coupling the two or more lead adaptors comprises electrically coupling each of the bi-atrial implantable leads to a lead adaptor that terminates each of the single pair of external cable lead elements.

25. The method according to claim 22, wherein the second cable portion of the patient safety medical device cable apparatus comprises a single pair of external cable lead elements, wherein the single pair of external cable lead elements corresponds to a single pair of bi-ventricular implantable leads, and further wherein electrically coupling the two or more lead adaptors comprises electrically coupling each of the bi-ventricular leads to a lead adaptor that terminates each of the single pair of external cable lead elements.

26. The method according to claim 22, wherein the second cable is portion of the patient safety medical device cable apparatus comprises two pairs of external cable lead elements, wherein the two pairs of external cable lead elements correspond to a single pair of bi-atrial implantable leads and a single pair of bi-ventricular implantable leads, and further wherein electrically coupling the two or more lead adaptors comprises electrically coupling each of the bi-atrial and bi-ventricular implantable leads to a lead adaptor that terminates each of the two pairs of external cable lead elements.

27. The method according to claim 22, wherein the external medical device is at least one of an external pacemaker, a programmer, and an analyzer.

28. The method according to claim 22, wherein attaching the external lead connector assembly to the external medical device comprises:

attaching the external lead connector assembly to an external medical device adaptor; and attaching the external medical device adaptor to the external medical device.

* * * * *